United States Patent [19]

Moffett

[11] 4,028,356
[45] June 7, 1977

[54] TRIAZINOBENZODIAZEPINES

[75] Inventor: Robert Bruce Moffett, Kalamazoo, Mich.

[73] Assignee: The Upjohn Company, Kalamazoo, Mich.

[22] Filed: Feb. 9, 1976

[21] Appl. No.: 656,372

[52] U.S. Cl. .................. 260/248 AS; 260/247.5 C; 424/249

[51] Int. Cl.² ............. C07D 253/08; C07D 487/04

[58] Field of Search ............... 260/248 AS, 247.5 C

[56] References Cited
UNITED STATES PATENTS 3,818,003  6/1974  Szmuszkovicz .................... 260/248
3,933,816  1/1976  Szmuszkovicz .................... 260/248

Primary Examiner—John M. Ford
Attorney, Agent, or Firm—Hans L. Berneis

[57] ABSTRACT

Compounds of formula IV:

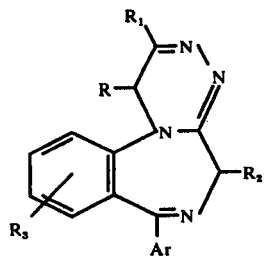

IV wherein R and $R_2$ are hydrogen or methyl; wherein $R_1$ is —COOH, —COOR' in which R' is alkyl of 1 to 3 carbon atoms, inclusive, —$(C_nH_{2n})$A in which $n$ is an integer of 1 to 3 and A is fluoro, chloro, bromo, trifluoromethyl, hydroxy, alkoxy, in which the alkyl group is defined as above, or

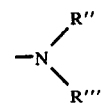

in which R'' and R''' are hydrogen or alkyl as defined above or together

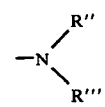

is pyrrolidino, piperidino, morpholino, 4-methylpiperazino, 4-(2-hydroxyethyl)-piperazino; wherein $R_3$ is hydrogen, fluoro, chloro, bromo, trifluoromethyl, or nitro; and wherein Ar is phenyl, o-chlorophenyl, o-fluorophenyl, 2,6-difluorophenyl, or 2-pyridyl, are produced.

The compounds of formula IV of this invention are sedatives, tranquilizers and muscle-relaxants and can be used for such purposes in mammals and birds.

21 Claims, No Drawings

TRIAZINOBENZODIAZEPINES

BACKGROUND OF THE INVENTION

Field of the Invention

This invention is concerned with new organic compounds and more particularly with triazinobenzodiazepines and methods for the production thereof.

The new products of this invention and the process of production thereof can be illustratively represented by the following formulae:

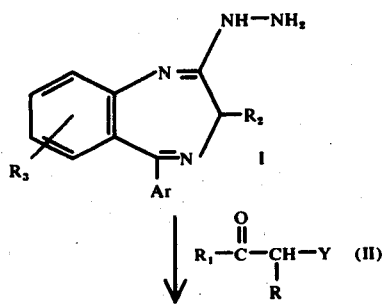

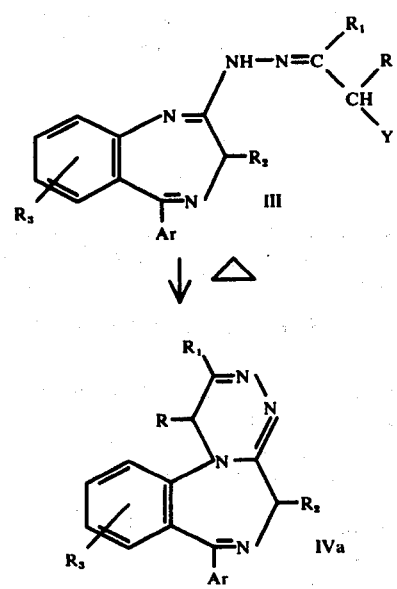

If $R_1$ is $-(CH_2)_n A'$ ($A'$ is X and X is chloro or bromo) and

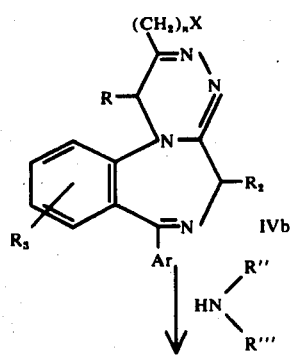

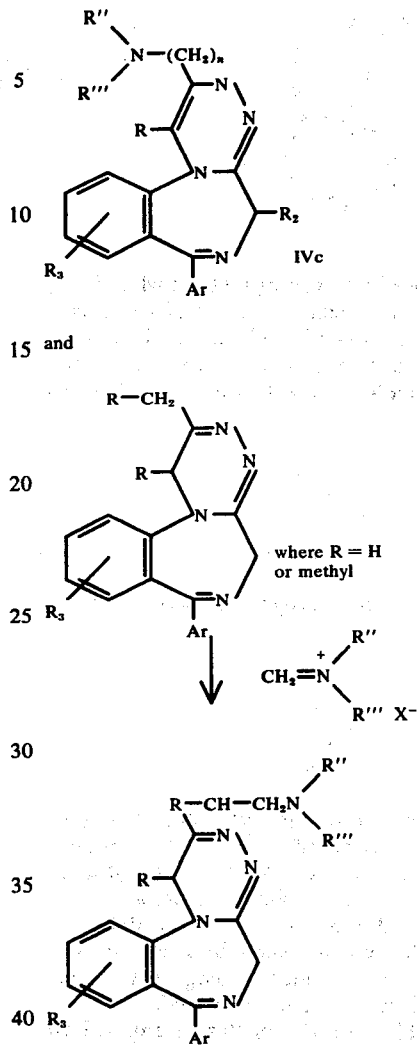

wherein R and $R_2$ are hydrogen or methyl; wherein $R_1$ is $-COOH$; $COOR'$, in which $R'$ is alkyl of 1 to 3 carbon atoms, inclusive, $-(C_nH_{2n})A$ in which A is fluoro, chloro, bromo, hydroxy, or alkoxy in which the alkyl group is defined as above; wherein $R_3$ is hydrogen, fluoro, chloro, bromo, trifluoromethyl, or nitro, and wherein Ar is phenyl, o-chlorophenyl, o-fluorophenyl, 2,6-difluorophenyl, or 2-pyridyl, and wherein X is chlorine or bromine, and wherein Y is chloro, bromo, iodo, or $-O-SO_2R_4$ ($R_4$ is alkyl of 1-3 carbon atoms, phenyl, or tolyl) and wherein $R''$ and $R'''$ are hydrogen or alkyl defined as above or together $$-N\begin{matrix}R''\\R'''\end{matrix}$$

is pyrrolidino, piperidino, morpholino, 4-methylpiperazino, or 4-(2-hydroxymethyl)piperazino.

The invention therefore comprises compounds of formula IV

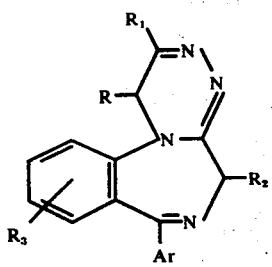

wherein R and R₂ are hydrogen or methyl; wherein $R_1$ is —COOH, COOR' in which R' is alkyl of 1 to 3 carbon atoms, inclusive, —(CnH₂n)A in which $n$ is an integer of 1 to 3 and A is fluoro, chloro, bromo, hydroxy, alkoxy in which the alkyl group is defined as above, or

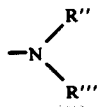

in which R'' and R''' are hydrogen or alkyl as defined above or together

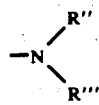

is pyrrolidino, piperidino, morpholino, 4-methylpiperazino, or 4-(2-hydroxyethyl)-piperazino; wherein $R_3$ is hydrogen, fluoro, chloro, bromo, trifluoromethyl, or nitro, and wherein Ar is phenyl, o-chlorophenyl, o-fluorophenyl, 2,6-difluorophenyl, or 2-pyridyl.

The invention also encompasses besides the compounds of formula IV, the pharmacologically acceptable acid addition salts of these compounds.

The more desirable products of this invention have the formula IVA

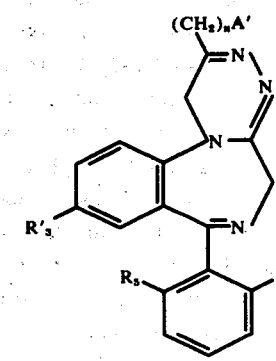

wherein A' is hydroxy or

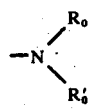

in which $R_o$ and $R'_o$ are hydrogen or alkyl of 1 to 3 carbon atoms, inclusive; wherein $n$ is an integer of 1 to 3; wherein $R'_3$ is hydrogen, chloro, fluoro, or trifluoromethyl; wherein $R_4$ is hydrogen, chloro, or fluoro; and wherein $R_5$ is hydrogen or fluoro with the proviso that $R_5$ is not fluoro if $R_4$ is chloro, and the pharmacologically acceptable acid addition salts thereof.

The most desirable compounds of this invention are of the formula IVB

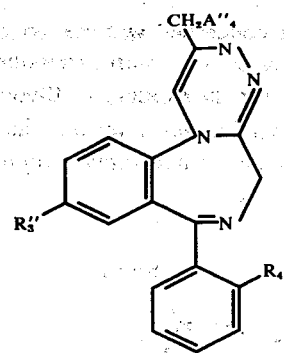

wherein A'' is hydroxy or dimethylamino, $R''_3$ and $R_4$ are hydrogen, chloro, or fluoro, and the pharmacologically acceptable acid addition salts thereof.

The process of the present invention comprises: treating a compound of formula I with a reagent of formula II to give the corresponding 2-(substituted-hydrazino)benzodiazepine III; and heating III to cyclize it and to provide the corresponding final product IV. If, as final product, a compound is desired wherein A is

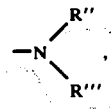

a compound wherein $R_1$ is —(CnH₂n)X in which $n$ is 1 to 3 and X is chloro or bromo can be reacted with a selected secondary amine in conventional manner.

DESCRIPTION OF THE PREFERRED EMBODIMENT

Alkyl groups of 1 to 3 carbon atoms, inclusive, are exemplified by methyl, ethyl, or propyl.

The novel compounds of the formula IV and pharmacologically acceptable addition salts thereof have sedative, hypnotic, anticonvulsant, tranquilizing and muscle relaxant effects in mammals and birds. Also as feed additives they increase growth rate and feed efficiency of livestock and poultry.

The pharmacologically acceptable acid addition salts of compounds of formula IV contemplated in this invention, are the hydrochlorides, hydrobromides, hydriodides, sulfates, phosphates, cyclohexanesulfamates, methanesulfonates, maleates, citrates, and the like, prepared by reacting a compound of formula IV with the selected pharmacologically acceptable acid.

Sedative effects of compounds of formula IV are shown by the following tests in mice:

Chimney test: [Med. Exp. 4, 145 (1961) ]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg). The control mice show overstimulation, i.e., (1) running convulsions followed by (2) tonic extensor fits; followed by (3) death. The intraperitoneal dosage of the test compound which protects 50% of the mice against (2) and (3) is the $ED_{50}$.

Antagonism to strychnine (as sulfate): The test consists in orally administering into groups of 6 mice the test compound, and 30 minutes later 3 mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice. A dosage which protects 50% of the mice from death is the $ED_{50}$.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring, and flavoring agents may be added.

For mammals and birds, food premixes, with starch, oatmeal, dried fishmeat, fishmeal, flour, and the like can be prepared.

As tranquilizer the compounds of formula IV and its pharmacologically acid addition salts can be used in dosages of 0.05–2.0 mg./kg., preferably 0.1 to 1.0 mg./kg. in oral or injectable preparations as described above, to alleviate tension and anxiety in mammals, or birds, such as e.g. occurs when animals are in travel.

Other acid addition salts of the compounds of formula IV can be made such as the fluosilicic acid addition salts which are useful mothproofing compounds or the trichloroacetates useful as herbicies against Johnson grass, Bermuda grass, yellow foxtail and green foxtail, and quack grass.

The starting compounds of formula I of this invention are synthesized as shown by Meguro et al., Tetrahedron Letters 4039 (1970).

The reactants of formula II are to a large extent commercially available, or can be made as shown by Catch et al., J. Chem. Soc., 1948, 278; Yu-hua et al., J. Gen. Chem. (USSR) 29, 3263 (1959); Arbuzov et al., J. Gen. Chem. (USSR) 32, 36-4 (1962); Magidson, et al., J. Gen. Chem (USSR) 29, 2803 (1959); Rodionov et al., Zhur. Obshahes Khim., 23, 1830 (1953); Bergman et al., J. Chem. Soc. 1958, 2259; Borowitz et al., J. Org. Chem., 34, 2687 (1969); Newberger et al., J. Chem. Soc. 1954, 1820.

In carrying out the process of this invention a selected compound I, dissolved in an inert organic solvent, is treated with a compound of formula II. Solvents useful in this reaction are tetrahydrofuran, dioxane, glyme, diglyme, ethanol, methanol, benzene, toluene, methylene, chloride, chloroform and the like. Temperatures for this reaction are between −20° to 80° C., preferably about room temperature (20 to 25° C). Temperatures above the melting point of the solvent should be used. The reactant II is used in a quantity of equimolecular to equimolecular +50% in relation to the starting benzodiazepine I. After the reaction is terminated the product III is recovered and purified in conventional manner e.g. evaporation of the mixture, extraction redissolving and filtering the impure product III, chromatography, and crystallization.

Product III is cyclized in a solvent preferably in tetrahydrofuran, but toluene, benzene, glyme, and diglyme can be used, at a temperature between 20° to 200° C., preferably between 25° to 125° C. Tetrahydrofuran is preferred since the product IVa formed under reflux conditions (about 65° C.) separates from the mixture as an acid addition salt and can be recovered by filtration. Compound IV is purified in conventional manner by chromatography and crystallization.

If other solvents are employed for the cyclization (for example, ethanol or methanol) compound IVa is obtained by conventional evaporation or conversion to the free base and extraction procedures and purified as above.

Compound IVa can also be obtained by increasing the pot temperature of the first step reaction, which will provide directly from compound I compound IVa without isolation of compound III.

If a compound of formula IVc is desired, a compound of formula IVb in which $R_1$ is —$(CnH_2n)X$ ($n$ is 1 to 3; X is chlorine or bromine) is treated with a secondary amine of the formula

in conventional manner.

Alternatively compounds of formula IVb (where $CnH_2nX$ is $CH_2Br$) can be obtained by the bromination of compounds IVb (where $CnH_2nX$ is $CH_3$) using, for example, N-bromosuccinimide.

Alternatively compounds of formula IVc (where $CnH_2n$ is R—CH—$CH_2$— (R is H or $CH_3$) can be obtained by the Mannich Reaction, for example by treating a compound of formula IVa ($R_1$ is methyl or ethyl) with

Other Mannich reagents

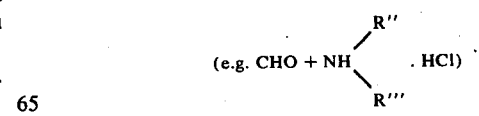

can be used (see Organic Reactions Vol. I, Page 303 and Vol. VII, page 99).

The following examples are illustrative of the processes and products of the present invention, but are not to be construed as limiting.

EXAMPLE 1

7-Chloro-2-[[2-chloro-1-(chloromethyl)ethylidene]-hydrazino]-5-phenyl-3H-1,4-benzodiazepine A solution of 4.7 g. (0.0165 mole) of 7-chloro-2-hydrazino-5-phenyl-3H-1,4-benzodiazepine in 83 ml. of tetrahydrofuran, under nitrogen, was cooled to 0° C. and a solution of 3.1 g. (0.025 mole) of 1,3-dichloropropanone-2 in 30 ml. of tetrahydrofuran was added dropwise during 40 minutes with stirring, and the solution was allowed to warm to room temperature. After 3.5 hours, thin layer chromatography of the reaction mixture (SiO$_2$, 10% methanol 90% chloroform) showed one spot moving much faster than the starting material. The solution was evaporated nearly to dryness in vacuo below room temperature, dissolved in 180 ml. of methylene chloride, filtered, concentrated to 90 ml., and diluted to 180 ml. with methanol. After cooling in the refrigerator, the crystals were collected, washed with methanol and dried, giving 2.10 g. of nearly white solid. Concentration of the filtrate below 20%, addition of more methanol to keep the volume at about 100 ml., and standing in the refrigerator gives 2.47 g. more product with identical infrared spectrum. The total yield was 4.57 g. (64.5%) of 7-chloro-2-[[2-chloro-1-(chloromethyl)ethylidene]hydrazino]-5-phenyl-3H-1,4-benzodiazepine.

Anal. calcd. for $C_{18}H_{15}Cl_3N_4$: C, 54.91; H, 3.84 Cl, 27.01; N, 14.23. Found: C, 54.66; H, 3.90; Cl, 27.07; N, 14.33.

EXAMPLE 2

7-Chloro-2-[[2-chloro-1-(chloromethyl)ethylidene]-hydrazino]-5-(o-chlorophenyl)-3H-1,4-benzodiazepine A solution of 3.19 g. (0.01 mole) of 7-chloro-5-o-chlorophenyl)-2-hydrazino-3H-1,4-benzodiazepine in 150 ml. of tetrahydrofuran, under nitrogen was cooled to 0° C. and 1.4 g. (0.011 mole) of 1,3L -dichloropropanone in 15 ml. of tetrahydrofuran was added dropwise with stirring. After stirring at 20° C. for ½ hour and at room temperature for 1.5 hours thin layer chromatography (SiO$_2$, 10% methanol/90% chloroform) showed essentially one spot, R$_f$ 7.4 as expected for the desired product, (starting material has R$_f$ 2.4). The solution was evaporated in vacuo below 25° C. giving light brown gum which solidified on trituration with ether to give 7-chloro-2-[[2-chloro-1-(chloromethyl)ethylidene]hydrazino]-5-(o-chlorophenyl)-3H-1,4-benzodiazepine.

EXAMPLE 3

2-[[2-Chloro-1-(chloromethyl)ethylidene]-hydrazino]-5-(o-chlorophenyl)-3H-1,4-benzodiazepine In the manner given in Example 1, 2-hydrazino-5-(o-chlorophenyl)-3-H-1,4-benzodiazepine in tetrahydrofuran can be treated with 1,3-dichloropropanone under nitrogen to give 2-[[2-chloro-1-(chloromethyl)ethylidene]-hydrazino]-5-(o-chlorophenyl)-3H-1,4-benzodiazepine.

EXAMPLE 4

7-Chloro-2-[[2-bromo-1-(bromomethyl)ethylidene]-hydrazino]-5-(o-fluorophenyl)-3H-1,4-benzodiazepine In the manner given in Example 1, 7-chloro-2-hydrazino-5-(o-fluorophenyl)-3H-1,4-benzodiazepine in tetrahydrofuran can be treated with 1,3-dibromopropanone under nitrogen to give 7-chloro-2-[[2-bromo-1-(bromomethyl)ethylidene]hydrazino]-5-(o-fluorophenyl)-3H-1,4-benzodiazepine.

EXAMPLE 5

7-Bromo-2-[[2-bromo-1-(chloromethyl)ethylidene]-hydrazino]-5-(2-pyridyl)-3H-1,4-benzodiazepine In the manner given in Example 1, 7-bromo-2-hydrazino-5-(2-pyridyl)-3H-1,4-benzodiazepine in tetrahydrofuran can be treated with 1-bromo-3-chloropropanone under nitrogen to give 7-bromo-2-[[2-bromo-1-(chloromethyl)ethylidene]hydrazino]-5-(2-pyridyl)-3H-1,4-benzodiazepine.

EXAMPLE 6

7-Chloro-2-[[2-chloro-1-(hydroxymethyl)ethylidene]-hydrazino]-5-phenyl-3H-1,4-benzodiazepine In the manner given in Example 1, 7-chloro-2-hydrazino-5-phenyl-3H-1,4-benzodiazepine in tetrahydrofuran can be treated with 1-chloro-3-hydroxypropanone under nitrogen to give 7-chloro-2-[[2-chloro-1-(hydroxymethyl)ethylidene]hydrazino]-5-phenyl-3H-1,4-benzodiazepine.

EXAMPLE 7

7-Chloro-2-[[2-chloro-1-(hydroxymethyl)ethylidene]-hydrazino]-5-(o-chlorophenyl)-3H-1,4-benzodiazepine In the manner given in Example 1,7-chloro-2-hydrazino-5-(o-chlorophenyl)-3H-1,4-benzodiazepine in tetrahydrofuran can be treated with 1-chloro-3-hydroxypropanone under nitrogen to give 7-chloro-2-[[2-chloro-1-(hydroxymethyl)ethylidene]hydrazino]-5-(o-chlorophenyl)-3H-1,4-benzodiazepine.

EXAMPLE 8

2-[[2-Bromo-1-(hydroxymethyl)ethylidene]-hydrazino]-5-(o-chlorophenyl)-3H-1,4-benzodiazepine In the manner given in Example 1,2-hydrazino-5-(o-chlorophenyl)-3H-1,4-benzodiazepine in tetrahydrofuran can be treated with 1-bromo-3-hydroxypropanone under nitrogen to give 2-[[2-bromo-1-(hydroxymethyl)ethylidene]-hydrazino]-5-(o-chlorophenyl)-3H-1,4-benzodiazepine.

EXAMPLE 9

7-Chloro-2-[[2-chloro-1-(hydroxymethyl)ethylidene]-hydrazino]-5-(o-fluorophenyl)-3H-1,4-benzodiazepine In the manner given in Example 1,7-chloro-2-hydrazino-5-(o-fluorophenyl)-3H-1,4-benzodiazepine in tetrahydrofuran can be treated with 1-chloro-3-hydroxypropanone under nitrogen to give 7-chloro-2-[[2-chloro-1-(hydroxymethyl)ethylidene]hydrazino]-5-(o-fluorophenyl)-3H-1,4-benzodiazepine.

EXAMPLE 10

7-Bromo-2-[[2-chloro-1-(hydroxymethyl)-ethylidene]hydrazino]-5-phenyl-3H-1,4-benzodiazepine

In the manner given in Example 1,7-bromo-2-hydrazino-5-phenyl-3H-1,4-benzodiazepine in tetrahydrofuran can be treated with 1-chloro-3-hydroxypropanone under nitrogen to give 7-bromo-2-[[2-chloro-1-(hydroxymethyl)ethylidene]hydrazino]-5-phenyl-3H-1,4-benzodiazepine.

EXAMPLE 11

7-Chloro-2-[[2-bromo-1-(trifluoromethyl)ethylidene]-hydrazino]-5-phenyl-3H-1,4-benzodiazepine

In the manner given in Example 1, 7-chloro-2-hydrazino-5-phenyl-3H-1,4-benzodiazepine in tetrahydrofuran can be treated with 1,1,1-trifluoro-3-bromopropanone under nitrogen to give 7-chloro-2-[[2-bromo-1-(trifluoromethyl)ethylidene]hydrazino]-5-phenyl-3H-1,4-benzodiazepine.

EXAMPLE 12

7-Nitro-2-[[2-chloro-1-(hydroxymethyl)ethylidene]-hydrazino]-5-phenyl-3H-1,4-benzodiazepine

In the manner given in Example 1, 7-nitro-2-hydrazino-5-phenyl-3H-1,4-benzodiazepine in tetrahydrofuran can be treated with 1-chloro-3-hydroxypropanone under nitrogen to give 7-nitro-2[[2-chloro-1-(hydroxymethyl)ethylidene]hydrazino]-5-phenyl-3H-1,4-benzodiazepine.

EXAMPLE 13

7-(Trifluoromethyl)-2-[[2-bromo-1-(hydroxymethyl)ethylidene]hydrazino]-5-phenyl-3H-1,4-benzodiazepine

In the manner given in Example 1, 7-(trifluoromethyl)-2-hydrazino-5-phenyl-3H-1,4-benzodiazepine in tetrahydrofuran can be treated with 1-bromo-3-hydroxypropanone under nitrogen to give 7-(trifluoromethyl)-2-[[2-bromo-1-(hydroxymethyl)ethylidene]hydrazino]-5-phenyl-3H-1,4-benzodiazepine.

EXAMPLE 14

7-Chloro-2-[[2-chloro-1-(2-hydroxy-2-methylpropyl)ethylidene]hydrazino]-5-phenyl-3H-1,4-benzodiazepine

In the manner given in Example 1, 7-chloro-2-hydrazino-5-phenyl-3H-1,4-benzodiazepine in tetrahydrofuran can be treated with 1-bromo-4-hydroxy-4-methyl-2-pentanone under nitrogen to give 7-chloro-2[[2-chloro-1-(2-hydroxy-2-methylpropyl)ethylidene]hydrazino]-5-phenyl-3H-1,4-benzodiazepine.

EXAMPLE 15

7-Chloro-2-[[2-chloro-1-(3-chloropropyl)ethylidene]-hydrazino]-5-(o-chlorophenyl)-3H-1,4-benzodiazepine

In the manner given in Example 1, 7-chloro-2-hydrazino-5-(0-chlorophenyl)-3H-1,4-benzodiazepine in tetrahydrofuran can be treated with 1,5-dichloro-2-pentanone under nitrogen to give 7-chloro-2-[[2-chloro-1-(3-chloropropyl)ethylidene]hydrazino]-5-(o-chlorophenyl)-3H-1,4-benzodiazepine.

EXAMPLE 16

7-Fluoro-2-[[2-bromo-1-(ethoxymethyl)ethylidene]-hydrazino]-5-(o-fluorophenyl)-3H-1,4-benzodiazepine

In the manner given in Example 1, 7-fluoro-2-hydrazino-5-(o-fluorophenyl)-3H-1,4-benzodiazepine in tetrahydrofuran can be treated with 1-chloro-3-ethoxypropanone under nitrogen to give 7-fluoro-2-[[2-bromo-1-(ethoxymethyl)ethylidene]hydrazino]-5-(o-fluorophenyl)-3H-1,4-benzodiazepine.

EXAMPLE 17

7-Nitro-2-[[2-bromo-1-(2-carbethoxyethyl)ethylidene]hydrazino]-5-phenyl-3H-1,4-benzodiazepine

In the manner given in Example 1, 7-nitro-2-hydrazino-5-phenyl-3H-1,4-benzodiazepine in tetrahydrofuran can be treated with ethyl 5-chloro-4-oxopentanoate under nitrogen to give 7-nitro-2-[[2-bromo-1-(carbethoxyethyl)ethylidene]hydrazino]-5-phenyl-3H-1,4-benzodiazepine.

EXAMPLE 18

7-Chloro-2-[[2-chloro-1-(fluoromethyl)ethylidene]hydrazino]-5-(o-chlorophenyl)-3H-1,4-benzodiazepine

In the manner given in Example 1, 7-chloro-2-hydrazino-5-(o-chlorophenyl)-3H-1,4-benzodiazepine in tetrahydrofuran can be treated with 1-chloro-3-fluoropropanone under nitrogen to give 7-chloro-2-[[2-chloro-1-(fluoromethyl)ethylidene]hydrazino]-5-(o-chlorophenyl)-3H-1,4-benzodiazepine.

EXAMPLE 19

7-Chloro-2-[[2-hydroxy-1-(3-carbomethoxypropyl)ethylidene]hydrazino]-5-phenyl-3H-1,4-benzodiazepine, methanesulfonate ester

In the manner given in Example 1, 7-chloro-2-hydrazino-5-phenyl-3H-1,4-benzodiazepine in tetrahydrofuran can be treated with 5-carbomethoxy-2-oxopentyl methanesulfonate under nitrogen to give 7-chloro-2-[[2-hydroxy-1-(3-carbomethoxypropyl)ethylidene]hydrazino]-5-phenyl-3H-1,4-benzodiazepine, methanesulfonate ester.

EXAMPLE 20

7-Fluoro-2-[[2-chloro-1-(hydroxymethyl)-propylidene]hydrazino]-5-phenyl-3H-1,4-benzodiazepine

In the manner given in Example 1, 7-fluoro-2-hydrazino-5-phenyl-3H-1,4-benzodiazepine in tetrahydrofuran can be treated with 3-chloro-1-hydroxy-2-butanone under nitrogen to give 7-fluoro-2-[[2-chloro-1-(hydroxymethyl)propylidene]hydrazino]-5-phenyl-3H-1,4-benzodiazepine.

EXAMPLE 21

7-(Trifluoromethyl)-2-[[2-chloro-1-(chloroethyl)ethylidene]hydrazino]-5-phenyl-3H-1,4-benzodiazepine

In the manner given in Example 1, 7-(trifluoromethyl)-2-hydrazino-5-phenyl-3H-1,4-benzodiazepine in tetrahydrofuran can be treated with 1,4-dichloro-2-butanone under nitrogen to give 7-(trifluoromethyl)-2-[[2-chloro-1-(2-chloroethyl)ethylidene]hydrazino]-5-phenyl-3H-1,4-benzodiazepine.

EXAMPLE 22

7-Chloro-2-[[2-chloro-1-(4-hydroxybutyl)ethylidene]-hydrazino]-5-(2,6-difluorophenyl)-3H-1,4-benzodiazepine In the manner given in Example 1, 7-chloro-2-hydrazino-5-(2,6-difluorophenyl)-3H-1,4-benzodiazepine in tetrahydrofuran can be treated with 1-chloro-6-hydroxy-2-hexanone under nitrogen to give 7-chloro-2-[[2-chloro-1-(4-hydroxybutyl)ethylidene]hydrazino]-5-(2,6-difluorophenyl)-3H-1,4-benzodiazepine.

EXAMPLE 23

7-Chloro-2-[[2-chloro-1-(2-chloroethyl)ethylidene]-hydrazino]-5-phenyl-3H-1,4-benzodiazepine In the manner given in Example 1, 7-chloro-2-hydrazino-5-phenyl-3H-1,4-benzodiazepine in tetrahydrofuran can be treated with 1,4-dichloro-2-butanone under nitrogen to give 7-chloro-2-[[2-chloro-1-(2-chloroethyl)ethylidene]hydrazino]-5-phenyl-3H-1,4-benzodiazepine.

EXAMPLE 24

9-Chloro-2-(chloromethyl)-1,5-dihydro-7-phenyl-as-triazino[4,3-a][1,4]benzodiazepine hydrochloride A solution of 5.7 g. (0.02 mole) of 7-chloro-2-hydrazino-5-phenyl-3H-1,4-benzodiazepine in 100 ml. of tetrahydrofuran under nitrogen was cooled to 0° C. and a solution of 2.8 g. (0.022 mole) of 1,3-dichloropropanone-2 in 25 ml. of tetrahydrofuran was added dropwise during 15 minutes. The solution was allowed to warm to room temperature and remain at room temperature for 14 days. After concentration to 100 ml., the resulting solid was collected giving 4.66 g. of tan solid. This was recrystallized from methanol, with treatment with activated charcoal (Darco G-60), yielding 3.3 g. (44%) of 9-chloro-2-(chloromethyl)-1,5-dihydro-7-phenyl-as-triazino[4,3-a][1,4]benzodiazepine of melting point 215°–260° C. with decomposition and darkening from 218° C. up.

Anal. calcd. for $C_{18}H_{14}Cl_2N_4 \cdot HCl$: C, 54.91; H, 3.84; Cl, 27.01; N, 14.23. Found: C, 54.61; H, 3.92; Cl, 27.13; N, 14.17.

A solution of 0.394 g. (0.001 mole) of 7-chloro-2-[[2-chloro-1-(chloromethyl)ethylidene]hydrazino]-5-phenyl-3H-1,4-benzodiazepine in 20 ml. of tetrahydrofuran under nitrogen, was stirred at room temperature for 7 days. The resulting precipitate was collected, washed with tetrahydrofuran and dried, yielding 0.08 g. (20.3%) of a tan solid. Ir was same as for the analyzed sample of 9-chloro-2-(chloromethyl)-1,5-dihydro-7-phenyl-as-triazino[4,3-a][1,4]benzodiazepine hydrochloride.

EXAMPLE 25

9-Chloro-2-(chloromethyl)-1,5-dihydro-7-(o-chlorophenyl)-as-triazino[4,3-a][1,4]benzodiazepine hydrochloride A solution of 7-chloro-2-[[2-chloro-1-(chloromethyl)ethylidene]hydrazino]-5-(o-chlorophenyl)-3H-1,4-benzodiazepine, prepared in situ in tetrahydrofuran as in Example 2 from 3.19 g. (0.01 mole) of 7-chloro-5-(o-chlorophenyl)-2-hydrazino-3H-1,4-benzodiazepine, was stirred under reflux in a nitrogen atmosphere for 3 hours during which time the solvent is allowed to boil off to concentrate the solution to 75 ml. After standing at room temperature overnight the resulting crystalline hydrochloride was collected washed with tetrahydrofuran and dried giving 1.54 g. (36%) of tan solid. This was dissolved in methanol, treated at the boiling point with activated charcoal, filtered, concentrated to 27 ml. and cooled yielding 0.65 g. of 9-chloro-2-(chloromethyl)-1,5-dihydro-7-(o-chlorophenyl)-as-triazino[4,3-a][1,4]benzodiazepine hydrochloride of melting point 230°–240° C. (dec.).

Anal. calcd. for $C_{18}H_{13}Cl_3N_4 \cdot HCl$: C, 50.50; H, 3.36; Cl, 33.12; N, 13.09. Found: C, 50.57; H, 3.24; Cl, 33.05; N, 13.04.

The hydrochloric acid addition salt can be treated in water with aqueous sodium bicarbonate solution until neutral, and the free base extracted with methylene chloride. Evaporation of the methylene chloride solution gives 9-chloro-2-(chloromethyl)-1,5-dihydro-7-phenyl-as-triazino[4,3-a][1,4]benzodiazepine.

EXAMPLE 26

2-(Chloromethyl)-1,5-dihydro-7-(o-chlorophenyl)-as-triazino[4,3-a][1,4]benzodiazepine and its hydrochloride In the manner given in Example 24, 2-[[2-chloro-1-(chloromethyl)ethylidene]hydrazino]-5-(o-chlorophenyl)-3H-1,4-benzodiazepine in tetrahydrofuran can be stirred to give 2-(chloromethyl)-1,5-dihydro-7-(o-chlorophenyl)-as-triazino[4,3-a][1,4]benzodiazepine as the hydrochloride. The free base can be obtained as described in Example 25.

EXAMPLE 27

9-Chloro-2-(bromomethyl)-1,5-dihydro-7-(o-fluorophenyl)-as-triazino[4,3-a][1,4]benzodiazepine and its hydrobromide In the manner given in Example 25, 7-chloro-2-[[2-bromo-1-(bromomethyl)ethylidene]hydrazino]-5-(o-fluorophenyl)-3H-1,4-benzodiazepine in tetrahydrofuran can be refluxed to give 9-chloro-2-(bromomethyl)-1,5-dihydro-7-(o-fluorophenyl)-as-triazino[4,3-a][1,4]benzodiazepine as the hydrobromide. The free base can be obtained as described in Example 25.

EXAMPLE 28

9-Bromo-2-(chloromethyl)-1,5-dihydro-7-(2-pyridyl)-as-triazino[4,3-a][1,4]benzodiazepine and its hydrochloride In the manner given in Example 24, 7-bromo-2-[[2-bromo-1-(chloromethyl)ethylidene]hydrazino]-5-(2-pyridyl)-3H-1,4-benzodiazepine in tetrahydrofuran can be stirred to give 9-bromo-2-(chloromethyl)-1,5-dihydro-7-(2-pyridyl)-as-triazino[4,3-a][1,4]benzodiazepine as the hydrobromide. The free base can be obtained as described in Example 25.

EXAMPLE 29

9-Chloro-2-(hydroxymethyl)-1,5-dihydro-7-phenyl-as-triazino[4,3-a][1,4]benzodiazepine and its hydrochloride In the manner given in Example 24, 7-chloro-2-[[2-chloro-1-(hydroxymethyl)ethylidene]hydrazino]-5-phenyl-3H-1,4-benzodiazepine in tetrahydrofuran can be stirred to give 9-chloro-2-(hydroxymethyl)-1,5-dihydro-7-phenyl-as-triazino[4,3-a][1,4]benzodiazepine was the hydrochloride. The free base can be obtained as described in Example 25.

EXAMPLE 30

9-Chloro-2-(hydroxymethyl)-1,5-dihydro-7-(o-chlorophenyl)-as-triazino[4,3-a][1,4]benzodiazepine and its hydrochloride In the manner given in Example 25, 7-chloro-2-[[2-chloro-1-(hydroxymethyl)ethylidene]hydrazino]-5-(o-chlorophenyl)-3H-1,4-benzodiazepine in tetrahydrofuran can be refluxed to give 9-chloro-2-(hydroxymethyl)-1,5-dihydro-7-(o-chlorophenyl)-as-triazino[4,3-a][1,4]benzodiazepine as the hydrochloride. The free base can be obtained as described in Example 25.

EXAMPLE 31

2-(Hydroxymethyl)-1,5-dihydro-7-(o-chlorophenyl)-as-triazino[4,3-a][1,4]benzodiazepine and its hydrobromide In the manner given in Example 25, 2-[[2-bromo-1-(hydroxymethyl)ethylidene]hydrazino]-5-(o-chlorophenyl)-3H-1,4-benzodiazepine in tetrahydrofuran can be refluxed to give 2-(hydroxymethyl)-1,5-dihydro-7-(o-chlorophenyl)-as-triazino[4,3-a][1,4]benzodiazepine as the hydrobromide. The free base can be obtained as described in Example 25.

EXAMPLE 32

9-Chloro-2-(hydroxymethyl)-1,5-dihydro-7-(o-fluorophenyl)-as-triazino[4,3-a][1,4]benzodiazepine and its hydrochloride In the manner given in Example 25, 7-chloro-2-[[2-chloro-1-(hydroxymethyl)ethylidene]hydrazino]-5-(o-fluorophenyl)-3H-1,4-benzodiazepine in tetrahydrofuran can be refluxed to give 9-chloro-2-(hydroxymethyl)-1,5-dihydro-7-(o-fluorophenyl)-as-triazino[4,3-a][1,4]benzodiazepine as the hydrochloride. The free base can be obtained as described in Example 25.

EXAMPLE 33

9-Bromo-2-(hydroxymethyl)-1,5-dihydro-7-phenyl-as-triazino[4,3-a][1,4]benzodiazepine and its hydrochloride.

In the manner given in Example 24, 7-bromo-2-[[2-chloro-1-(hydroxymethyl)ethylidene]hydrazino]-5-phenyl-3H-1,4-benzodiazepine in tetrahydrofuran can be stirred to give 9-bromo-2-(hydroxymethyl)-1,5-dihydro-7-phenyl-as-triazino[4,3-a][1,4]benzodiazepine as the hydrochloride. The free base can be obtained as described in Example 25.

EXAMPLE 34

9-Chloro-2-(trifluoromethyl)-1,5-dihydro-7-phenyl-as-triazino[4,3-a][1,4]benzodiazepine and its hydrobromide In the manner given in Example 25, 7-chloro-2-hydrazino-5-phenyl-3H-1,4-benzodiazepine in tetrahydrofuran can be treated with 3-bromo-1,1,1-trifluoropropanone and refluxed to give 9-chloro-2-(trifluoromethyl)-1,5-dihydro-7-phenyl-as-triazino[4,3-a][1,4]benzodiazepine as the hydrobromide. The free base can be obtained as described in Example 25.

EXAMPLE 35

9-Nitro-2-(hydroxymethyl)-1,5-dihydro-7-phenyl-as-triazino[4,3-a][1,4]benzodiazepin and its hydrochloride.

In the manner given in Example 25, 7-nitro-2-[[2-chloro-1-(hydroxymethyl)ethylidene]hydrazino]-5-phenyl-3H-1,4-benzodiazepine in benzene can be refluxed to give 9-nitro-2-(hydroxymethyl)-1,5-dihydro-7-phenyl-as-triazino[4,3-a][1,4]benzodiazepine as the hydrochloride. The free base can be obtained as described in Example 25.

EXAMPLE 36

9-Trifluoromethyl)-2-(hydroxymethyl)-1,5-dihydro-7-phenyl-as-triazino[4,3-a][1,4]benzodiazepine and its hydrobromide In the manner given in Example 24, 7-(trifluoromethyl)-2-[[2-bromo-1-(hydroxymethyl)ethylidene]hydrazino]-5-phenyl-3H-1,4-benzodiazepine in glyme can be stirred to give 9-(trifluoromethyl)-2-(hydroxymethyl)-1,5-dihydro-7-phenyl-as-triazino[4,3-a][1,4]benzodiazepine as the hydrobromide. The free base can be obtained as described in Example 25.

EXAMPLE 37

9-Chloro-2-(2-hydroxyethyl)-1,5-dihydro-7-phenyl-as-triazino[4,3-a][1,4]benzodiazepine and its hydrochloride In the manner given in Example 24, 7-chloro-2-[[2-chloro-1-(2-hydroxyethyl)ethylidene]hydrazino]-5-phenyl-3H-1,4-benzodiazepine in diglyme can be stirred to give 9-chloro-2-(2-hydroxyethyl)-1,5-dihydro-7-phenyl-as-triazino[4,3-a[1,4]benzodiazepine as the hydrochloride. The free base can be obtained as described in Example 25.

EXAMPLE 38

9-Chloro-2(3-chloropropyl)-1,5-dihydro-7-(o-chlorophenyl)-as-triazino[4,3-a][1,4]benzodiazepine and its hydrochloride In the manner given in Example 24, 7-chloro-2-[[2-chloro- 1-(3-chloropropyl)ethylidene]hydrazino]-5-(o-chlorophenyl)-3H-1,4-benzodiazepine in methanol can be stirred to give 9-chloro-2-(3-chloropropropyl)-1,5-dihydro-7-(o-chlorophenyl)-as-triazino[4,3-a][1,4]benzodiazepine as the hydrochloride. The free base can be obtained as described in Example 25.

EXAMPLE 39

9-Fluoro-2-(methoxymethyl)-1,5-dihydro-7-(o-fluorophenyl)-as-triazino[4,3-a][1,4]benzodiazepine and its hydrobromide In the manner given in Example 24, 7-fluoro-2-[[2-bromo-1-(ethoxymethyl)ethylidene]hydrazino]-5-(o-fluorophenyl)-3H-1,4-benzodiazepine in toluene can be stirred to give 9-fluoro-2-(ethyoxymethyl)-1,5-dihydro-7-(o-fluorophenyl)-as-triazino[4,3-a][1,4]benzodiazepine as the hydrobromide. The free base can be obtained as described in Example 25.

EXAMPLE 40

9-Nitro-2-(2-carboethoxyethyl)-1,5-dihydro-7-phenyl-as-triazino[4,3-a][1,4]benzodiazepine and its hydrochloride In the manner given in Example 25, 7-nitro-2-hydrazino-5-phenyl-3H-1,4-benzodiazepine in glyme can be treated at 0° with ethyl 5-chlorolevulinate and then refluxed to give 9-nitro-2-(2-carbethoxyethyl)-1,5-dihydro-7-phenyl-as-triazino[4,3-a][1,4]benzodiazepine as the hydrochloride. The free base can be obtained as described in Example 25.

EXAMPLE 41

9-Chloro-2-(fluoromethyl)-1,5-dihydro-7-(o-chlorophenyl)-as-triazino[4,3-a][1,4]benzodiazepine and its hydrochloride In the manner given in Example 24, 7-chloro-2-[[2-(chloro-1-(fluoromethyl)ethylidene]hydrazino]-5-(o-chlorophenyl)-3H-1,4-benzodiazepine in dioxane can be stirred to give 9-chloro-2-(fluoromethyl)-1,5-dihydro-7-(o-chlorophenyl)-as-triazino[4,3-a][1,4]benzodiazepine as the hydrochloride. The free base can be obtained as described in Example 25.

EXAMPLE 42

9-Chloro-2-(3-carbomethoxypropyl)-1,5-dihydro-7-phenyl-as-triazino[4,3-a][1,4]benzodiazepine and its methansulfonate In the manner given in Example 25, 7-chloro-2-[[2-hydroxy-1-(3-carbomethoxypropyl)ethylidene]hydrazino]-5-phenyl-3H-1,4-benzodiazepine methanesulfonate in tetrahydrofuran can be refluxed to give 9-chloro-2-(3-carbomethoxypropyl)-1,5-dihydro-7-phenyl-as-triazino[4,3-a]-[1,4]benzodiazepine as the methanesulfonate (salt). The free base can be obtained as described in Example 25.

EXAMPLE 43

9-Fluoro-2-(hydroxymethyl)-1-methyl-1,5-dihydro-7-phenyl-as-triazino[4,3-a][1,4]benzodiazepine and its hydrochloride.

In the manner given in Example 24, 7-fluoro-2-[[2-chloro-1-(hydroxymethyl)propylidene]hydrazino]-5-phenyl-3H-1,4-benzodiazepine in tetrahydrofuran can be stirred to give 9-fluoro-2-(hydroxymethyl)-1-methyl-1,5-dihydro-7-phenyl-as-triazino[4,3-a][1,4]benzodiazepine as the hydrochloride. The free base can be obtained as described in Example 25.

EXAMPLE 44

9-(Trifluoromethyl)-2-(2-chloroethyl)-1,5-dihydro-7-phenyl-as-triazino[4,3-a][1,4]benzodiazepine and its hydrochloride In the manner given in Example 24, 7-(trifluoromethyl)-2-[[2-chloro-1-(2-chloroethyl)ethylidene]hydrazino]-5-phenyl-3H-1,4-benzodiazepine in tetrahydrofuran can be stirred to give 9-(trifluoromethyl)-2-(2-bromoethyl)-1,5-dihydro-7-phenyl-as-triazino[4,3-a][1,4]benzodiazepine as the hydrochloride. The free base can be obtained as described in Example 25.

EXAMPLE 45

9-Chloro-2-(3-hydroxypropyl)-1,5-dihydro-7-(2,6-difluorophenyl)-as-triazino[4,3-a][1,4]benzodiazepine and its hydrochloride In the manner given in Example 25, 7-chloro-2-[[2-chloro-1-(3-hydroxypropyl) ethylidene]hydrazino]-5-(2,6-difluorophenyl)-3H-1,4-benzodiazepine in tetrahydrofuran can be refluxed to give 9-chloro-2-(3-hydroxypropyl)-1,5-dihydro-7-(2,6-difluorophenyl)-as-triazino[4,3-a][1,4]benzodiazepine as the hydrochloride. The free base can be obtained as described in Example 25.

EXAMPLE 46

9-Chloro-2-(2-chloroethyl)-1,5-dihydro-7-phenyl-as-triazino[4,3-a][1,4]benzodiazepine and its hydrochloride In the manner given in Example 24, 7-chloro-2-[[2-chloro-1-(2-chloroethyl)ethylidene]hydrazino]-5-phenyl-3H-1,4-benzodiazepine in tetrahydrofuran can be stirred to give 9-chloro-2-(2-chloroethyl)-1,5-dihydro-7-phenyl-as-triazino[4,3-a][1,4]benzodiazepine as the hydrochloride. The free base can be obtained as described in Example 25.

EXAMPLE 47

9-Chloro-2-carbethoxy-1,5-dihydro-7-phenyl-as-triazino[4,3-a][1,4]benzodiazepine, hydrobromide To a solution of 2.85 g. (0.01 mole) of 7-chloro-2-hydrazino-5-phenyl-3H-1,4-benzodiazepine in 75 ml of tetrahydrofuran under nitrogen was added 2.0 ml (0.0257 mole) of ethyl bromopyruvate. The solution became dark and a solid soon separated. After standing for 5 days the solid was collected, washed with tetrahydrofuran and dried giving 2.07 g. of tan solid, melting point 205°–215° C. (decomp). This solid was dissolved in 250 ml. of ethanol, treated at the boiling point with activated charcoal, filtered and concentrated until crystallization started (about 180 ml.). After standing overnight the crystals were collected, washed with ethanol and dried yielding 0.95 g. (20.3%) of 9-chloro-2-carbethoxy-1,5-dihydro-7-phenyl-as-triazino[4,3-a][1,4]benzodiazepine, hydrobromide of melting point 216°–223° C. (decomp. with darkening from 205° up).

Anal. calcd. for $C_{20}H_{18}BrClN_4O_2$: C, 52.02; H, 3.93; Br, 17.31; Cl, 7.68; N, 12.13. Found: C, 51.93; H, 4.14; Br, 17.53; Cl, 7.07. (by difference from total halogen); N, 12.19.

EXAMPLE 48

9-Chloro-2-carboxy-1,5-dihydro-7-phenyl-as-triazino[4,3-a][1,4]benzodiazepine hydrochloride In the manner given in Example 47, 7-chloro-2-hydrazino-5-phenyl-3H-1,4-benzodiazepine in tetrahydrofuran can be stirred with chloropyruvic acid to give 9-chloro-2-carboxy-1,5-dihydro-7-phenyl-as-triazino-[4,3-a]benzodiazepine as the hydrochloride.

EXAMPLE 49

9-Chloro-2-[(dimethylamino)methyl]-1,5-dihydro-7-phenyl-as-triazino[4,3-a][1,4]benzodiazepine To a solution of 1.87 g. (0.005 mole) of 9-chloro-2-(chloromethyl)-1,5-dihydro-7-phenyl-as-triazino[4,3-a]-[1,4]benzodiazepine hydrochloride in 250 ml. of methanol and 40 ml. of water was added, under nitrogen, with stirring 10 ml., (0.5 mole) of 20% aqueous dimethylamine. After stirring at room temperature for 5 hours the solution was evaporated in vacuo below 37° C. The residue was dissolved in methylene chloride and washed with dilute aqueous sodium hydroxide, twice with water, and then with sodium chloride solution. After drying over anhydrous sodium sulfate and filtering, the methylene chloride solution was evaporated to dryness in vauco. The residue was dissolved in 25 ml. of 2-propanol, filtered, concentrated to 20 ml. and cooled giving 0.93 g. (59%) of 9-chloro-2-[(dimethylamino)methyl]-1,5-dihydro-7-phenyl-as-triazino[4,3-a][1,4]benzodiazepine of melting point 169°–190° C. with decomposition and darkening from 150° up.

Anal. calcd. for $C_{20}H_{20}ClN_5$: C, 65.55; H, 5.51; Cl, 9.69; N, 19.14. Found: C, 65.57; H, 5.65; Cl, 9.70; N, 18.83.

EXAMPLE 50

9-Chloro-7-(o-chlorophenyl)-2-[(dimethylamino(methyl]-1,5-dihydro-as-triazino[4,3-a][1,4]benzodiazepine To a solution of 0.856 g. (0.002 mole) of 9-chloro-2-(chloromethyl)-7-(o-chlorophenyl)-1,5-dihydro-as-triazino[4,3-a][1,4]benzodiazepine hydrochloride in 100 ml. of methanol, under nitrogen, was added slowly with stirring 4 ml. (0.02 mole) of 2.5% aqueous dimethylamine. After stirring for 6 hours at room temperature and standing at 3° C. overnight the solution was evaporated in vacuo below 35° C. giving a light brown gum. This gum was dissolved in methylene chloride, washed with water, sodium chloride solution, and dried over anhydrous sodium sulfate. After filtration and evaporation of the solvent the product was triturated with ether, collected and dried yielding 0.6 g. of tan solid. This solid was dissolved in 700 ml. of ether at the boiling point, filtered, and concentrated to 50 ml. After cooling the product was collected, washed with ether and dried yielding 0.4 g. (50%) of yellow crystals of 9-chloro-7-(o-chlorophenyl)-2-[(dimethylamino)methyl]-1,5-dihydro-as-triazino[4,3-a][1,4]benzodiazepine of melting point 170°–174° C. (decomp.).

Anal. calcd. for $C_{20}H_{19}Cl_2N_5$: C, 60.01; H, 4.78; Cl, 17.71; N, 17.50; Found: C, 59.97; H, 4.70; Cl, 17.33; N, 16.63.

EXAMPLE 51

2-(Methylaminomethyl)-1,5-dihydro-7-(o-chlorophenyl)-as-triazino[4,3-a][1,4]benzodiazepine In the manner given in Example 49, 2-(chloromethyl)-1,5-dihydro-7-(o-chlorophenyl)-as-triazino[4,3-a][1,4]-benzodiazepine can be reacted with aqueous methylamine to give 2-(methylaminomethyl)-1,5-dihydro-7-(o-chlorophenyl)-as-triazino[4,3-a][1,4]benzodiazepine.

EXAMPLE 52

9-Chloro-2-(aminomethyl)1,5-dihydro-7-(o-fluorophenyl)-as-triazino[4,3-a][1,4]benzodiazepine In the manner given in Example 49, 9-chloro-2-(bromomethyl)-1,5-dihydro-7-(o-fluorophenyl)-as-triazino-[4,3-a][1,4]benzodiazepine can be reacted with aqueous ammonia to give 9-chloro-2-(aminomethyl)-1,5-dihydro-7-(o-fluorophenyl)-as-triazino[4,3-a][1,4]benzodiazepine.

EXAMPLE 53

9-Bromo-2-[(dimethylamino)methyl]-1,5-dihydro-7-(2-pyridyl)-as-triazino[4,3-a][1,4]benzodiazepine In the manner given in Example 49, 9-bromo-2-(chloromethyl)-1,5-dihydro-7-(2-pyridyl)-as-triazino[4,3-a][1,4]benzodiazepine can be reacted with aqueous dimethylamine to give 9-bromo-2-[(dimethylamino)methyl]-1,5-dihydro-7-(2-pyridyl)-as-triazino[4,3-a][1,4]benzodiazepine.

EXAMPLE 54

9-Chloro-2-[(diethylamino)methyl]-1,5-dihydro-7-phenyl-as-triazino[4,3-a][1,4]benzodiazepine In the manner given in Example 49, 9-chloro-2-(chloromethyl)-1,5-dihydro-7-phenyl-as-triazino[4,3-a][1,4]benzodiazepine can be reacted with diethylamine to give 9-chloro-2-[(diethylamino)methyl]-1,5-dihydro-7-phenyl-as-triazino[4,3-a][1,4]benzodiazepine.

EXAMPLE 55

9-Chloro-2-[(methylamino)methyl]-1,5-dihydro-7-(o-chlorophenyl)-as-triazino[4,3-a][1,4]benzodiazepine In the manner given in Example 49, 9-chloro-2-(chloromethyl)-1,5-dihydro-7-(o-chlorophenyl)-as-triazino[4,3-a][1,4]benzodiazepine can be reacted with aqueous monomethylamine to given 9-chloro-2-[(methylamino)methyl]-1,5-dihydro-7-)o-chlorophenyl)-as-triazino[4,3-a][1,4]benzodiazepine.

EXAMPLE 56

9-Chloro-2-[2-(dimethylamino)ethyl]-1,5-dihydro-7-phenyl-as-triazino[4,3-a][1,4]benzodiazepine In the manner given in Example 49, 9-chloro-2-(2-bromoethyl)-1,5-dihydro-7-phenyl-as-triazino[4,3-a][1,4]benzodiazepine can be reacted with aqueous dimethylamine to given 9-chloro-2-[2-(dimethylamino)ethyl]-1,5-dihydro-7-phenyl-as-triazino[4,3-a][1,4]benzodiazepine.

EXAMPLE 57

9-Chloro-2-(pyrrolidinomethyl)-1,5-dihydro-7-phenyl-as-triazino[4,3-a][1,4]benzodiazepine In the manner given in Example 49, 9-chloro-2-(chloromethyl)-1,5-dihydro-7-phenyl-as-triazino[4,3-a][1,4]benzodiazepine can be reacted with pyrrolidine to give 9-chloro-2-(pyrrolidinomethyl)-1,5-dihydro-7-phenyl-as-triazino[4,3-a][1,4]benzodiazepine.

EXAMPLE 58

9-(trifluoromethyl)-2-(piperidinomethyl)-1,5-dihydro-7-phenyl-as-triazino[4,3-a][1,4]benzodiazepine In the manner given in Example 49, 9-(trifluoromethyl)-2-(bromomethyl)-1,5-dihydro-7-phenyl-as-triazino[4,3-a][1,4]benzodiazepine can be reacted with piperidine to give 9-(trifluoromethyl)-2-(piperidinomethyl)-1,5-dihydro-7-phenyl-as-triazino[4,3-a][1,4]benzodiazepine.

EXAMPLE 59

9-Fluoro-2-[(4-methylpiperazino)methyl]-1,5-dihydro-7-(o-fluorophenyl)-as-triazino[4,3-a][1,4]benzodiazepine In the manner given in Example 49, 9-fluoro-2-(chloromethyl)-1,5-dihydro-7-(o-fluorophenyl)-as-triazino[4,3-a][1,4]benzodiazepine can be reacted with 4-methylpiperazine to give 9-fluoro-2-[(4-methylpiperazino)methyl]-1,5-1,5-dihydro-7-(o-fluorophenyl)-as-triazino[4,3-a][1,4]benzodiazepine.

EXAMPLE 60

9-Chloro-2-[[4-(2-hydroxyethyl)piperazino]methyl]-1,5-dihydro-7-(o-chlorophenyl)-as-triazino[4,3-a][1,4]benzodiazepine In the manner given in Example 49, 9-chloro-2-(chloromethyl)-1,5-dihydro-7-(o-chlorophenyl)-as-triazino[4,3-a][1,4]benzodiazepine can be reacted with 4-(2-hydroxyethyl)piperazine to give 9-chloro-2-[[4-(2-hydroxyethyl)piperazino]methyl]-1,5-dihydro-7-(o-chlorophenyl)-as-triazino[4,3-a][1,4]benzodiazepine.

EXAMPLE 61

9-(Trifluoromethyl)-2-[(methylethylamino)methyl]-1,5-dihydro-7-phenyl-as-triazino[4,3-a][1,4]benzodiazepine In the manner given in Example 49, 9-(trifluoromethyl)-2-(chloromethyl)-1,5-dihydro-7-phenyl-as-triazino[4,3-a][1,4]benzodiazepine can be reacted with methylethylamine to give 9-(trifluoromethyl)-2-[(methylethylamino)methyl]-1,5-dihydro-7-phenyl-as-triazino[4,3-a][1,4]benzodiazepine.

EXAMPLE 62

9-Nitro-2-[(methylpropylamino)methyl]-1,5-dihydro-7-(o-fluorophenyl)-as-triazino[4,3-a][1,4]benzodiazepine In the manner given in Example 49, 9-nitro-2-(bromomethyl)-1,5-dihydro-7-(o-fluorophenyl)-as-triazino[4,3-a][1,4]benzodiazepine can be reacted with methylpropylamine to given 9-nitro-2-[(methylpropylamino)methyl]-1,5-dihydro-7-(o-fluorophenyl)-as-triazino[4,3-a][1,4]benzodiazepine.

EXAMPLE 63

9-Chloro-2-[(2-dimethylamino)ethyl]-1,5-dihydro-7-phenyl-as-triazino[4,3-a][1,4]benzodiazepine A. 9-Chloro-1,5-dihydro-2-methyl-7-phenyl-as-triazino[4,3-a][1,4]benzodiazepine A solution of 2.85 g. (0.01 mole) of 7-chloro-2-hydrazino-5-phenyl-3H-1,4-benzodiazepine in 75 ml. of tetrahydrofuran, under nitrogen, was cooled to 0° C. and 1 ml. (1.15 g., 0.0124 mole) of chloropropanone was added during 10 minutes with stirring. Stirring at 0° C. is continued for 0.5 hours and then allowed to warm to room temperature and stirred for 2 hours. The mixture was then evaporated in vacuo at room temperature. The residue was dissolved in 150 ml. of warm ethyl acetate, filtered hot, concentrated to 50 ml. and cooled to give 2.93 g. (79%) of 7-chloro-2-[[(2-chloro-1-methyl)ethylidene]hydrazino]-5-phenyl-3H-1,4-benzodiazepine of melting point 210°–227° C. (decomposition with darkening from 160° C. up).

Anal. calcd. for $C_{18}H_{26}Cl_2N_4$: C, 60.18; H, 4.49; Cl, 19.74; N, 15.60. Found: C, 59.92; H, 4.53; Cl, 19.39; N, 15.49.

A soltuion of 0.72 g. (0.002 mole) of the hydrazone from A in 25 ml. of toluene, under nitrogen was stirred under reflux for 4 hours. After standing overnight the resulting crystals were collected and washed with toluene and ether and dried, giving 0.32 g. of a brown solid. This solid was dissolved in 20 ml. of methanol, treated at the boiling point with decolorizing charcoal, filtered, concentrated by a stream of nitrogen on a steam bath to about 5 ml. and diluted with 2-propanol. Concentration was continued until crystallization started. After cooling, the product was collected, washed with 2-propanol and ether and dried to yield 0.2 g. (28%) of 9-chloro-1,5-dihydro-2-methyl-7-phenyl-as-triazino[4,3-a][1,4]benzodiazepine hydrochloride of melting point 235°–245° C. (decomposition with darkening from 213° C. up).

Anal. calcd. for $C_{18}H_{16}Cl_2N_4$: C, 60.18; H, 4.49; Cl, 19.74; N, 15.60. Found: C, 60.08; H, 4.53; Cl, 19.58; N, 15.82.

The hydrochloride from above was mixed with dilute aqueous sodium hydroxide and extracted with chloroform. The chloroform extract was dried over magnesium sulfate, filtered and evaporated in vacuo to give 0.6 g. of brown crystalline solid. This was dissolved in chloroform, treated with decolorizing charcoal, filtered, concentrated and diluted with ether. After standing for 3 hours the product was collected, washed with ether and dried to give 0.35 g. (22%) of 9-chloro-1,5-dihydro-2-methyl-7-phenyl-as-triazino[4,3-a][1,4]benzodiazepine. Melt solvate showed presence of chloroform of crystallization (0.0471 mole/mole) based on chlorine analysis.

Anal. calcd. for $C_{18}H_{15}ClN_4 \cdot 0.0471$ $CHCl_3$ C, 66.01; H, 4.62; Cl, 12.32; N, 17.06. Found: C, 65.94; H, 4.67; Cl, 12.32; N, 17.41.

A solution of 0.154 g. (0.0015 mole) of tetramethyldiaminomethane is dimethylformamide under nitrogen is cooled in an ice bath and 0.1 ml. of acetyl chloride is added slowly with stirring. To this slurry of dimethyl(methylene)ammonium chloride can be added 0.01 mole of 9-chloro-1,5-dihydro-2-methyl-7-phenyl-as-triazino[4,3-a][1,4]benzodiazepine. The mixture can be stirred at room temperature until tlc ($SiO_2$, 10% MeOH/$CHCl_3$) indicates the reaction is complete. The product can be isolated as a hydrochloride by dilution of the reaction mixture with ether and filtration or alternatively the reaction mixture can be cooled, basified with sodium carbonate, extracted with chloroform and the free base chromatographed yielding 9-chloro-2-[(2-dimethylamino)ethyl]-1,5-dihydro-7-phenyl-as-triazino[4,3-a][1,4]benzodiazepine.

EXAMPLE 64

9-Chloro-7-(o-chlorophenyl)-2-[(2-dimethylamino)ethyl]-1,5-dihydro-as-triazino[4,3-a][1,4]benzodiazepine A. 9-Chloro-7-(o-chlorophenyl)-1,5-dihydro-2-methyl-as-triazino[4,3-a][1,4]benzodiazepine hydrochloride A mixture of 3.19 g. (0.01 mole) of 7-chloro-5-(o-chlorophenyl)-2-hydrazino-3H-1,4-benzodiazepine and 100 ml. of tetrahydrofuran under nitrogen was cooled to 0° C. and 1 ml. of chloropropanone was slowly added with stirring. The mixture was allowed to warm to room temperature and after ½ hour, the solution was evaporated at room temperature in vacuo to given a light brown gum which was dissolved in absolute ether and filtered. The solution was concentrated on a steam bath to a small volume and pentane was added. After cooling in the refrigerator, the resulting crystals were collected, washed with ether and pentane and dried, yielding 3.82 g. (97%) of 7-chloro-2-[[(2-chloro-1-methyl)ethylidene]hydrazino]-5-(o-chlorophenyl)-3H-1,4-benzodiazepine, melting point 202°–217° with decomposition and darkening from 120° up. A sample for analysis was recrystallized from isopropanol giving the same ir and melting behavior.

Anal. calcd. for $C_{18}H_{15}Cl_3N_4$: C, 54.91; H, 3.84; Cl, 27.01; N, 14.23. Found: C, 54.62; H, 4.13; Cl, 27.35; N, 14,23.

A soltuion of 3.15 g. (0.008 mole) of the hydrazone from above in 50 ml. of toluene, under nitrogen was stirred under reflux for 2.5 hours and allowed to stand for 3 days. The resulting solid was collected giving 1.78 g. of brown crystals. This was dissolved in 60 ml. of methanol, treated at the boiling point with decolorizing charcoal (Darco G-60), filtered, and concentrated to 15 ml. Dilution at boiling point to 50 ml. with absolute ether and cooling yielded 1.22 g. (38.8%) of 9-chloro-7-(o-chlorophenyl)-1,5-dihydro-2-methyl-as-triazino[4,3-a][1,4]benzodiazepine hydrochloride, melting point 250°–260° C. with decomposition from 225° C. up.

Anal. calcd. for $C_{18}H_{14}Cl_2N_4$: C, 54.91; H, 3.84; Cl, 27.01; N, 14.23. Found: C, 54.75; H, 4.09; Cl, 26.94; N, 14.33.

The free base can be liberated from the hydrochloride by basifying with aqueous sodium carbonate, extracting with chloroform and evaporating the extract.

In the manner given in Example 63 a slurry of dimethyl(methylene)ammonium chloride in dimethylformamide can be treated with 9-chloro-7-(o-chlorophenyl)-1,5-dihydro-2-methyl-as-triazino[4,3-a][1,4]benzodiazepine and stirred at room temperature to give 9-chloro-7-(o-chlorophenyl)-2-[(2-dimethylamino)ethyl]-1,5-dihydro-as-triazino[4,3-a][1,4]benzodiazepine.

EXAMPLE 65

9-Chloro-2-(bromomethyl)-1,5-dihydro-7-phenyl-as-triazino[4,3-a][1,4]benzodiazepine A mixture of 0.001 mole of 9-chloro-1,5-dihydro-2-methyl-7-phenyl-as-triazino[4,3-a][1,4]benzodiazepine and 0.0011 mole of N-bromosuccinimide in carbon tetrachloride, under nitrogen, can be stirred under reflux until tlc indicates the reaction is complete. The product can be isolated by neutralization with aqueous sodium bicarbonate, extraction with methylene chloride and chromatographing on silica gel to give 9-chloro-2-bromomethyl-1,5-dihydro-7-phenyl-as-triazino[4,3-a][1,4]benzodiazepine.

EXAMPLE 66

9-Chloro-2-(bromomethyl)-1,5-dihydro-7-(o-chlorophenyl)-as-triazino[4,3-a][1,4]benzodiazepine In the manner given in Example 65, 9-chloro-1,5-dihydro-2-methyl-7-(o-chlorophenyl)-as-triazino[4,3-a][1,4]benzodiazepine can be mixed with N-bromosuccinimide and carbon tetrachloride and stirred under reflux to give 9-chloro-2-(bromomethyl)-1,5-dihydro-7-(o-chlorophenyl)-as-triazino[4,3-a][1,4]benzodiazepine.

In the manner given in Example 1, other 2-[[2-halo-1-substituted ethylidene]hydrazino]-5-phenyl-3H-1,4-benzodiazepines can be obtained. Representative compounds thus obtained include:

7-chloro-2-[[2-chloro-1-carboxyethylidene]hydrazino]-5-phenyl-3H-1,4-benzodiazepine;
8-fluoro-2-[[2-chloro-1-(chloromethyl)ethylidene]hydrazino]-5-(o-chlorophenyl)-3H-1,4-benzodiazepine;
7-nitro-2-[[2-chloro-1-(chloromethyl)ethylidene]hydrozino]-5-(o-chlorophenyl)-3H-1,4-benzodiazepine;
7-nitro-2-[[2-bromo-1-(hydroxymethyl)ethylidene]hydrazino]-5-(o-chlorophenyl)-3H-1,4-benzodiazepine;
6-nitro-2-[[2-bromo-1-(hydroxymethyl)ethylidene]hydrazino]-5-(o-chlorophenyl-3H-1,4-benzodiazepine;
9-trifluoromethyl-2-[[2-bromo-(hydroxymethyl)ethylidene]hydrazino]-5-(o-fluorophenyl)-3H-1,4-benzodiazepine;
7-trifluoromethyl-2-[[2-chloro-1-(chloroethyl)ethylidene]hydrazino]-5-(o-chlorophenyl)-3H-1,4-benzodiazepine;
7-fluoro-2-[[2-chloro-1-(chloromethyl)ethylidene]hydrazino]-5-(2,6-difluorophenyl)-3H-1,4-benzodiazepine;
8-fluoro-2-[[2-chloro-1-(carboxyethyl)ethylidene]hydrazino]-5-(o-chlorophenyl)-3H-1,4-benzodiazepine;
9-fluoro-2-[[2-bromo-1-(carboxypropyl)ethylidene]hydrazino]-5-phenyl-3H-1,4-benzodiazepine;
7-bromo-2-[[2-chloro-1-(2-hydroxy-2-methylpropyl)ethylidene]hydrazino]-5-phenyl-3H-1,4-benzodiazepine;
8-bromo-2-[[2-bromo-1-(hydroxymethylpropylidene)]hydrazino]-5-(2,6-difluorophenyl)-3H-1,4-benzodiazepine;
2-[[2-chloro-1-(3-carbomethoxypropyl)ethylidene]hydrazino]-5-(o-chlorophenyl)-3H-1,4-benzodiazepine;
2-[[2-bromo-1-(hydroxymethyl)ethylidene]hydrazino]-5-(o-chlorophenyl)-3H-1,4-benzodiazepine;
2-[[2-chloro-1-carboxyethylidene]hydrazino]-5-(o-chlorophenyl)-3H-1,4-benzodiazepine;
7-fluoro-2-[[2-chloro-1-carboxyethylidene]hydrazino]-5-(o-chlorophenyl)-3H-1,4-benzodiazepine;
and the like.

In the manner given in Example 24, other 2-substituted-1,5-dihydro-7-phenyl-as-triazino[4,3-a][1,4]benzodiazepines can be prepared. Representative compounds thus obtained, include:

10-fluoro-2-chloromethyl-1,5-dihydro-7-(o-chlorophenyl)-as-triazino[4,3-a][1,4]benzodiazepine;
9-nitro-2-chloromethyl-1,5-dihydro-7-(o-chlorophenyl)-as-triazino[4,3-a][1,4]benzodiazepine;
9-nitro-2-hydroxymethyl-1,5-dihydro-7-(o-chlorophenyl)-as-triazino[4,3-a][1,4]benzodiazepine;
8-nitro-2-hydroxymethyl-1,5-dihydro-7-(o-chlorophenyl)-as-triazino[4,3-a][1,4]benzodiazepine;
11-trifluoromethyl-2-hydroxymethyl-1,5-dihydro-7-(o-chlorophenyl)-as-triazino[4,3-a][1,4]benzodiazepine;

9-trifluoromethyl-2-chloroethyl-1,5-dihydro-7-(o-chlorophenyl)-as triazino[4,3-a][1,4]benzodiazepine;
9-fluoro-2-chloromethyl-1,5-dihydro-7-(2,6-difluorophenyl)-as-triazino[4,3-a][1,4]benzodiazepine;
10-fluoro-2-carboxyethyl-1,5-dihydro-7-(o-chlorophenyl)-as-triazino[4,3-a][1,4]benzodiazepine;
11-fluoro-2-carboxypropyl-1,5-dihydro-7-phenyl-as-triazino[4,3-a][1,4]benzodiazepine;
9-bromo-2-(2-hydroxy-2-methylpropyl)-1,5-dihydro-7-phenyl-as-triazino[4,3-a][1,4]benzodiazepine;
10-bromo-2-(2-hydroxyethyl)-1,5-dihydro-7-(2,6-difluorophenyl)-as-triazino[4,3-a][1,4]benzodiazepine;
2-(3-carbomethoxypropyl)-1,5-dihydro-7-(o-chlorophenyl)-as-triazino[4,3-a][1,4]benzodiazepine;
2-hydroxymethyl-1,5-dihydro-7-(o-chlorophenyl)-as-triazino[4,3-a][1,4]benzodiazepine;
2-carboxy-1,5-dihydro-7-(o-chlorophenyl)-as-triazino[4,3-a][1,4]benzodiazepine;
8-fluoro-2-carboxy-1,5-dihydro-7-(o-chlorophenyl)-as-triazino[4,3-a][1,4]benzodiazepine;
and the like.

In the manner given in Example 49, 2-aminoalkyl-1,5-dihydro-7-phenyl-as-triazino[4,3-a][1,4]benzodiazepines can be synthesized from the corresponding 2-chloroalkyl-1,5-dihydro-7-phenyl-as-triazino[4,3-a][1,4,]benzodiazepine and a secondary amine. Representative compounds, thus produced, include:

10-fluoro-2-[(dimethylamino)methyl]-1,5-dihydro-7-(o-chlorophenyl)-as-triazino[4,3-a][1,4]benzodiazepine;
10-fluoro-2-[(diethylamino)methyl]-1,5-dihydro-7-(o-chlorophenyl)-as-triazino[4,3-a][1,4]benzodiazepine;
10-fluoro-2-(pyrrolidinomethyl)-1,5-dihydro-7-(o-chlorophenyl)-as-triazino[4,3-a][1,4]benzodiazepine;
10-fluoro-2-[(4-methylpiperazino)methyl]-1,5-dihydro-7-(o-chlorophenyl)-as-triazino[4,3-a][1,4]benzodiazepine;
9-nitro-2-[(dimethylamino)methyl]-1,5-dihydro-7-(o-chlorophenyl)-as-triazino[4,3-a][1,4]benzodiazepine;
9-nitro-2-[[4-[(2-hydroxyethyl)piperazino]methyl]-1,5-dihydro-(o-chlorophenyl)-as-triazino[4,3-a][1,4]benzodiazepine;
9-nitro-2-[(piperidino)methyl]-1,5-dihydro-7-(o-chlorophenyl)-as-triazino[4,3-a][1,4]benzodiazepine;
9-nitro-2-[(morpholino)methyl]-1,5-dihydro-7-(o-chlorophenyl)-as-triazino[4,3-a][1,4]benzodiazepine;
9-trifluoromethyl-2-[2-[(diethylamino)ethyl]]-1,5-dihydro-7-(o-chlorophenyl)-as-triazino[4,3-a][1,4]benzodiazepine;
9-trifluoromethyl-2-[2-(morpholino)ethyl]-1,5-dihydro-7-(o-chlorophenyl)-as-triazino[4,3-a][1,4]benzodiazepine;
9-trifluoromethyl-2-[2-(piperidino)ethyl]-1,5-dihydro-7-(o-chlorophenyl)-as-triazino[4,3-a][1,4]benzodiazepine;
9-trifluoromethyl-2-[2-(dipropylamino)ethyl]-1,5-dihydro-7-(o-chlorophenyl)-as-triazino[4,3-a][1,4]benzodiazepine;
9-fluoro-2-[di(isopropylamino)methyl]-1,5-dihydro-7-(2,6-difluorophenyl)-as-triazino[4,3-a][1,4]benzodiazepine;
2-[(diethylamino)methyl]-1,5-dihydro-7-(2,6-difluorophenyl)-as-triazino[4,3-a][1,4]benzodiazepine;
2-[[4-(2-hydroxyethyl)piperazino]methyl]-1,5-dihydro-7-(2,6-difluorophenyl)-as-triazino[4,3-a][1,4]benzodiazepine;
2-[(4-methylpiperazino)methyl]-1,5-dihydro-7-(2,6-difluorophenyl)-as-triazino[4,3-a][1,4]benzodiazepine; and the like.

The pharmacologically acceptable acid addition salts of compounds of formula IV can be prepared and isolated by conventional processes, such as reacting a compound of formula IV with a selected pharmacologically acceptable acid. Such acids include hydrochloric, hydrobromic, phosphoric, sulfuric, acetic, tartaric, lactic, citric, malic, maleic, methanesulfonic, benzenesulfonic, cyclohexanesulfamic acids, toluenesulfonic, and the like. The reaction is conveniently performed in an organic solvent, e.g., ether, dioxane, or tetrahydrofuran, ethanol, methanol, ethyl acetate; the salts can be recovered by crystallization, precipitation or evaporating the solvent. These salts are useful in the same manner as the free base.

I claim:

1. A compound of formula IV:

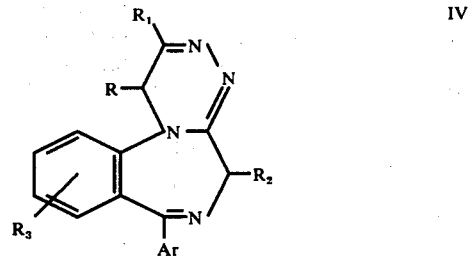

wherein R and $R_2$ are hydrogen or methyl; wherein $R_1$ is —COOH, —COOR' in which R' is alkyl or 1 to 3 carbon atoms (inclusive), —$(CH_2)_n$A in which $n$ is an integer of 1 to 3 and A is fluoro, chloro, bromo, trifluoromethyl, hydroxy, alkoxy in which the alkyl group is defined as above, or

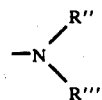

in which R'' and R''' are hydrogen or alkyl as defined above or together

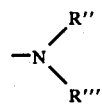

is pyrrolidino, piperidino, morpholino, 4-methylpiperazino, 4-(2-hydroxyethyl)piperazino; wherein $R_3$ is hydrogen, fluoro, chloro, bromo, trifluoromethyl, or nitro, and wherein Ar is phenyl, o-chlorophenyl, o-fluorophenyl, 2,6-difluorophenyl, or 2-pyridyl, and the pharmacologically acceptable acid addition salts thereof.

2. A compound according to claim 1 of the formula IVa:

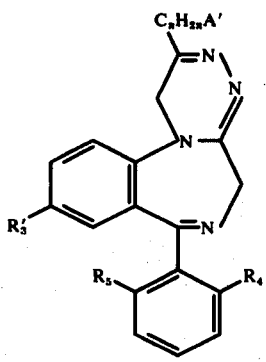

wherein A' is hydroxy or

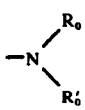

in which $R_o$ and $R'_o$ are hydrogen or alkyl of 1 to 3 carbon atoms inclusive; wherein n is an integer of 1 to 3; wherein $R'_3$ is hydrogen, chloro, fluoro, or trifluoromethyl; wherein $R_4$ is hydrogen, chloro, or fluoro; and wherein $R_5$ is hydrogen or fluoro with the proviso that $R_5$ is not fluoro if $R_4$ is chloro, and the pharmacologically acceptable acid addition salts thereof.

3. A compound according to claim 1 of the formula IVb:

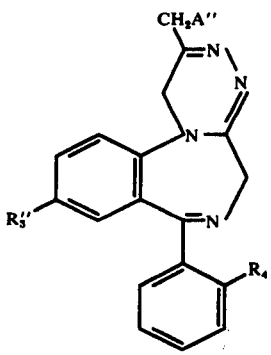

wherein A" is hydroxy or dimethylamino, $R''_3$ and $R_4$ are hydrogen, chloro, or fluoro, and the pharmacologically acceptable acid addition salts thereof.

4. A compound according to claim 3, wherein A" is hydroxy, $R_4$ is hydrogen, $R''_3$ is chloro and the compound is therefore 9-chloro-2-(hydroxymethyl)-1,5-dihydro-7-phenyl-as-triazino[4,3-a][1,4]benzodiazepine.

5. A compound according to claim 3, wherein A" is hydroxy, $R''_3$ and $R_4$ are chloro, and the compound is therefore 9-chloro-2-hydroxymethyl-1,5-dihydro-7-(o-chlorophenyl)-as-triazino[4,3-a][1,4]benzodiazepine.

6. A compound according to claim 3, wherein A is hydroxy, $R''_3$ and $R_4$ are hydrogen, and the compound is therefore 2-hydroxymethyl-1,5-dihydro-7-phenyl-as-triazino[4,3-a][1,4]benzodiazepine.

7. A compound according to claim 3, wherein A" is dimethylamino, $R''_3$ is chloro, $R_4$ is hydrogen and the compound is therefore 9-chloro-2-[(dimethylamino)-methyl]-1,5-dihydro-7-phenyl-as-triazino[4,3-a][1,4]benzodiazepine.

8. A compound according to claim 3, wherein A" is dimethylamino, $R''_3$ and $R_4$ are chloro, and the compound is therefore 9-chloro-2-[(dimethylamino)methyl]-1,5-dihydro-7-(o-chlorophenyl)-as-triazino[4,3-a][1,4]benzodiazepine.

9. A compound according to claim 3, wherein A" is dimethylamino, $R''_3$ is hydrogen, $R_4$ is chloro and the compound is therefore 2-[(dimethylamino)methyl]-1,5-dihydro-7-(o-chlorophenyl)-as-triazino[4,3-a][1,4]benzodiazepine.

10. A compound according to claim 3, wherein A" is dimethylamino, $R''_3$ is chloro, $R_4$ is fluoro, and the compound is therefore 9-chloro-2-[(dimethylamino)-methyl]-1,5-dihydro-7-(o-fluorophenyl)-as-triazino[4,3-a][1,4]benzodiazepine.

11. A compound according to claim 3, wherein A" is hydroxy, $R''_3$ is chloro, $R_4$ is fluoro, and the compound is therefore 9-chloro-2-hydroxymethyl-1,5-dihydro-7-((o-fluorophenyl)-as-triazino[4,3-a][1,4]benzodiazepine.

12. A compound according to claim 3, wherein A" is chloro, $R''_3$ is chloro, $R_4$ is hydrogen, and the compound is therefore 9-chloro-2-chloromethyl-1,5-dihydro-7-phenyl-as-triazino[4,3-a][1,4]benzodiazepine as the hydrochloride.

13. A compound according to claim 3, wherein A" is chloro, $R_4$ is chloro, $R''_3$ is hydrogen, and the compound is therefore 2-chloromethyl-1,5-dihydro-7-(o-chlorophenyl)-as-triazino[4,3-a][1,4]benzodiazepine.

14. A compound according to claim 1, wherein Ar is pyridyl, $R_1$ is hydroxymethyl, R and $R_2$ are hydrogen, $R_3$ is bromo, and the compound is therefore 9-bromo-2-hydroxymethyl-1,5-dihydro-7-(2-pyridyl)-as-triazino[4,3-a][1,4]benzodiazepine.

15. A compound according to claim 1, wherein Ar is pyridyl, R and $R_2$ are hydrogen, $R_1$ is [(dimethylamino)methyl], $R_3$ is 9-bromo and the compound is therefore 9-bromo-2-[(dimethylamino)methyl]-1,5-dihydro-7-(2-pyridyl)-as-triazino[4,3-a][1,4]benzodiazepine.

16. A process for the production of a compound IVa:

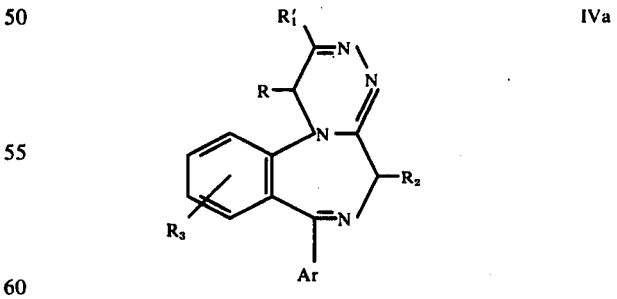

wherein R and $R_2$ are hydrogen or methyl; wherein $R'_1$ is —COOH, COOR' in which R' is alkyl of 1 to 3 carbon atoms (inclusive), —$(CH_2)_nA'$ in which A' is fluoro, chloro, bromo, trifluoromethyl, hydroxy, alkoxy in which the alkyl group is defined as above, which comprises: treating between −20° to 80° C. a compound of the formula I:

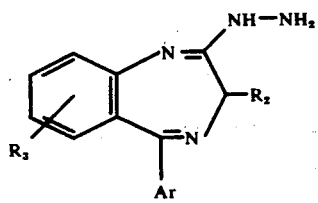

wherein $R_2$, $R_3$, and Ar are defined as above with a compound of the formula II:

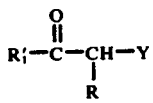

wherein $R'_1$ and R are defined as above and Y is chlorine, bromine, iodine, or $-O-SO_2R_4$ ($R_4$ is alkyl of 1–3 carbon atoms, phenyl, or tolyl) in an inert organic solvent, to give the compound III:

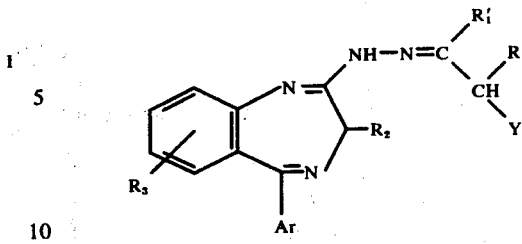

wherein Ar, R, $R'_1$, $R_2$, $R_3$, and Y are defined as above; and allowing to cyclize III at a temperature between 10° to 60° C., to obtain the corresponding compound of formula IVa.

17. The process of claim 16, wherein the starting compound is 7-chloro-2-hydrozino-5-phenyl-4H-1,4-benzodiazepine.

18. The process of claim 16, wherein the starting compound is 7-chloro-2-hydrazino-5-(o-chlorophenyl)-3H-1,4-benzodiazepine.

19. The process of claim 16, wherein the starting compound is 7-chloro-2-hydrazino-5-(2-pyridyl)-3H-1,4-benzodiazepine.

20. The process of claim 16, wherein the compound II is 1,3-dichloropropane.

21. The process of claim 16, wherein the compound II is 1-chloro-3-hydroxypropanone.

* * * * *

UNITED STATES PATENT AND TRADEMARK OFFICE
CERTIFICATE OF CORRECTION

PATENT NO. : 4,028,356
DATED : June 7, 1977
INVENTOR(S) : Robert Bruce Moffett

It is certified that error appears in the above-identified patent and that said Letters Patent are hereby corrected as shown below:

Column 26, line 23, "((o-fluoro" should read -- (o-fluoro --

*Signed and Sealed this*

*Thirty-first* Day of *July 1979*

[SEAL]

*Attest:*

*Attesting Officer*

LUTRELLE F. PARKER
*Acting Commissioner of Patents and Trademarks*